US005798320A

United States Patent [19]
Dawson et al.

[11] Patent Number: 5,798,320
[45] Date of Patent: Aug. 25, 1998

[54] GELATION ADDITIVE FOR HYDRAULIC FRACTURING FLUIDS

[75] Inventors: Jeffrey C. Dawson, Spring; Hoang Van Le, Houston, both of Tex.

[73] Assignee: BJ Services Company, Houston, Tex.

[21] Appl. No.: 939,963

[22] Filed: Sep. 29, 1997

Related U.S. Application Data

[63] Continuation of Ser. No. 858,652, May 19, 1997, abandoned, which is a continuation of Ser. No. 428,378, Apr. 25, 1995, abandoned.

[51] Int. Cl.$^6$ ............... C09K 3/00; C07F 7/00; E21B 43/17
[52] U.S. Cl. ............... 507/271; 507/244; 507/266; 507/267; 507/903; 507/922; 556/55; 525/370; 525/371; 166/308
[58] Field of Search ............... 507/244, 266, 507/271, 903, 922, 267; 556/55; 525/370, 371; 166/308

[56] References Cited

U.S. PATENT DOCUMENTS

| | | | |
|---|---|---|---|
| 4,460,751 | 7/1984 | Hanlon et al. | 507/244 |
| 4,524,829 | 6/1985 | Hanlon et al. | 507/244 |
| 4,606,772 | 8/1986 | Almond et al. | 166/294 |
| 4,664,713 | 5/1987 | Almond et al. | 166/294 |
| 4,686,052 | 8/1987 | Baranet et al. | |
| 4,798,902 | 1/1989 | Putzig | |
| 4,953,621 | 9/1990 | Putzig et al. | |
| 5,021,171 | 6/1991 | Smeltz | |
| 5,089,149 | 2/1992 | Ridland et al. | |
| 5,181,568 | 1/1993 | McKown et al. | 166/293 |
| 5,182,408 | 1/1993 | Sharif | 556/55 |
| 5,252,234 | 10/1993 | Sharif | |
| 5,322,123 | 6/1994 | Kohler et al. | |
| 5,466,846 | 11/1995 | Sharif | 556/55 |
| 5,478,802 | 12/1995 | Moradi-Araghi | 507/271 |

*Primary Examiner*—Philip Tucker
*Attorney, Agent, or Firm*—Arnold, White & Durkee

[57] ABSTRACT

A method of formulating a zirconium lactate compound is accomplished by combining in solution lactic acid or a lactate salt with zirconium carbonate. The reacting solution forms zirconium lactate and carbon dioxide which is evolved as a gas from the solution. This eliminates the need to filter or wash the zirconium lactate in order to remove undesirable by-products. The zirconium lactate can be used as a crosslinking agent for crosslinking aqueous polymer gels used in such things as fracturing fluids for fracturing subterranean formations of oil and gas wells.

17 Claims, No Drawings

GELATION ADDITIVE FOR HYDRAULIC FRACTURING FLUIDS

This application is a continuation of Ser. No. 858,652, filed May 19, 1997, abandoned, which is a continuation of application Ser. No. 08/428,378, filed Apr. 25, 1995, now abandoned.

BACKGROUND OF THE INVENTION

1. Field of the Invention:

This invention relates to a method of forming a zirconium compound from a starting material of zirconium carbonate, and in particular, to a method of forming zirconium lactate for use in crosslinking gelled fracturing fluids used in treating subterranean formations of oil and gas wells.

2. Description of the Prior Art:

Hydraulic fracturing fluids used in fracturing subterranean formations of oil and gas wells are usually formed from aqueous based fluids which are gelled by the addition of soluble polymers. These soluble polymers are often formed from solvatable polysaccharides which include such things as guar, guar derivatives and carboxylated cellulose. With very little addition of these polymers, the viscosity of the aqueous fluid can be increased dramatically. Increasing viscosity of these aqueous based fluids for use as fracturing fluids is beneficial for various reasons. High viscosity fluids create better, larger fractures within the formation when introduced under high pressure. The higher viscosity fluids are also better able to carry proppants which are dispersed throughout the fluid and forced into the fractures so that the fractures remain open after the fluid is removed.

Typically, less than 1% by weight of the soluble polymers are added to water to form these viscous aqueous fluids. At this concentration, water viscosity can be increased from about 1 cps to about 35 cps at 511 $sec^{-1}$ as measured using a Fann 50 viscometer. Further enhancement of the fluid viscosity occurs by the addition of crosslinking agents. These additives are able to bind polymer strands together to form a continuous network, thus further increasing the viscosity of the fluid. With the addition of these crosslinker additives, the viscosity of the aqueous fluids can be increased and exceed 500 cps at 170 $sec^{-1}$. These crosslinkers are generally formed using metal complexes of titanium, zirconium, aluminum or boron. The ligands associated with these metals are chosen so that once the complex is added to the aqueous polymer sol, the polymer must compete with the ligand for the metal. This is beneficial in that it ensures that the metal complex is homogeneously mixed in the polymer sol before crosslinking occurs. The delayed effect also results in less friction or back pressures while pumping the fluid at higher rates into the oil and gas wells.

Zirconium lactate is commonly used as a metallic crosslinker in crosslinking these aqueous polymer fluids. Zirconium lactate can provide delayed gelation and high viscosities at elevated temperatures for periods of time that are practical for hydraulic fracturing treatments in oil and gas wells. Prior art methods of formulating zirconium lactate typically involve mixing lactic acid to either zirconium hydroxychloride or zirconium oxychloride. These compounds react to form zirconium lactate as a white precipitate. To remove chloride by-products, the zirconium lactate product is filtered, washed and redissolved by neutralization with a suitable base. The base is generally sodium, potassium or ammonium hydroxide. This method of formulating zirconium lactate has disadvantages, however. Washing and filtering of the product usually results in less than 100% yield. As much as 10% $ZrO_2$ may be lost during washing. Wastewater from the washings must be recovered and properly disposed. The crosslinkers formed in this manner may be polymer specific and difficult to use with other polymers. These crosslinkers are also expensive because of the extensive processing and handling of wastewater that is required.

What is needed is a simple method of formulating zirconium lactate which does not generate waste or loss of product as a result of washing and separating techniques.

SUMMARY OF THE INVENTION

A zirconium compound is formulated by combining in solution an amount of an alpha-hydroxy carboxylic acid or salt of an alpha-hydroxy carboxylic acid, such as lactic acid, with an amount of zirconium carbonate. The solution is then allowed to react with carbon dioxide being given off as a by-product. The carbon dioxide is allowed to evolve from the solution as a gas so that the zirconium product does not need to be washed to remove undesirable by-products.

The zirconium compound produced can be used as a crosslinking agent for crosslinking viscous polymer gels, such as those used in fracturing fluids, by further neutralizing the aqueous solution so that zirconium precipitate is dissolved. The solution can then be added to the polymer fluid.

The novel features believed characteristic of the invention are set forth in the appended claims. The invention itself however, as well as a preferred mode of use, further objects and advantages thereof, will best be understood by reference to the following detailed description of an illustrative embodiment.

DETAILED DESCRIPTION OF THE PREFERRED EMBODIMENT

Although the invention has been described with reference to a specific embodiment, this description is not meant to be construed in a limiting sense. Various modifications of the disclosed embodiment as well as alternative embodiments of the invention will become apparent to persons skilled in the art upon reference to the description of the invention. It is therefore contemplated that the appended claims will cover any such modifications or embodiments that fall within the true scope of the invention.

A zirconium compound can be formed in a simple process by the addition of zirconium carbonate to an aqueous solution of an alpha-hydroxy carboxylic acid or salt of an alpha-hydroxy carboxylic acid. Suitable alpha-hydroxy carboxylic acids include lactic acid, malic acid and citric acid, with lactic acid being preferred. Suitable salts of the alpha-hydroxy carboxylic acids include the alkaline metal, ammonium and organoammonium salts, with lactate salts being preferred.

Because zirconium carbonate is used, the reaction results in a by-product of carbon dioxide. Thus, during the reaction, carbon dioxide is given off as a gas which simply bubbles out of solution so that filtering and washing of the zirconium product is unnecessary. It has been found, when reacting zirconium carbonate with either lactic acid or a lactate salt, that the best results are achieved when heating the solution at or above 200° F. for at least an hour. The amount of lactic acid or lactate salt used should exceed three moles per mole of zirconium. Preferably, 4 to 9 moles lactic acid or lactate salt to one mole of zirconium are used. At low pH, the zirconium lactate product formed appears as a precipitate. If desired, this precipitate can be removed from solution by filtering and dried for later use.

By further neutralizing the solution with a suitable base, the zirconium precipitate can be dissolved and used as a crosslinking additive for crosslinking various viscous aqueous gels used as fracturing fluids. For neutralization, the alkanolamines, particularly triethanolamine, have been found to be particularly well suited when forming zirconium lactate. It is believed that triethanolamine complexes with the metal, thus enhancing the crosslinking of the gel. Other suitable bases include potassium hydroxide and ammonium hydroxide. It is also possible to prevent precipitation of the zirconium product by maintaining an alkaline pH of the reacting solution.

When using the zirconium compound as a crosslinking agent for aqueous polymer gels used as fracturing fluids, a gelled polymer fracturing fluid is first prepared by adding between about 1% or less by weight of a soluble polymer such as guar, guar derivative or carboxylated cellulose to water. The zirconium crosslinking agent is then added to the gelled fluid in solution while mixing. Additionally, proppants and other additives, such as gel stabilizers, buffers, crosslink delaying agents and surfactants, may be added to the fluid prior to pumping into an oil or gas well. The fluid is then pumped into the well at a sufficiently high rate or pressure to cause fractures within the hydrocarbon bearing areas of the formation. The zirconium compound is particularly useful when treating high temperature wells, i.e. those having temperatures in excess of 200° F., due to the good thermal stability and retained viscosity of the crosslinked polymer gel.

The following examples further illustrate the method of formulating zirconium lactate and its performance when used to crosslink different polymer gels.

EXAMPLE 1

An aqueous solution was prepared using 31.26 g of an 85% aqueous lactic acid and 20 g of water. This solution was then heated to 200° F. and 20 g of zirconium carbonate (40% active as $ZrO_2$) was slowly added. The solution was stirred for 90 minutes during which time, 48 g of water was added to help suspend the precipitating solids. After the 90 minutes, 31.26 g of 99% by weight triethanolamine was slowly added to the slurry. The solids redissolved and were heated at 200° F. for another 30 minutes. The clear and colorless solution was then cooled to ambient temperatures. Zirconium content measured as $ZrO_2$ was 5.7% by weight. This solution was then used in carrying out further testing as a crosslinker.

EXAMPLE 2

Performance of the crosslinking was evaluated as part of a fracturing fluid. The polymer sol was prepared by hydrating 4.8 g of carboxymethyl hydroxypropyl guar (CMHPG) in one liter of a 2% weight per volume (wt/vol) potassium chloride solution, which is equivalent to 20 g of potassium chloride per liter of water. The potassium chloride was added to the fracturing fluids to minimize formation damage. After hydrating for 30 minutes, 1.2 g of thiosulfate, gel stabilizer, and one ml of 48% potassium carbonate buffer was added. While agitating the fluid, 0.75 ml of the crosslinker, prepared from Example 1, was added. The fluid was then sheared for 60 seconds without appreciable increases in viscosity.

The polymer fluid was then tested by pouring 42.0 g of the fluid into a Fann 50 viscometer cup. The cup was screwed onto the viscometer and pressurized to 200 psi with nitrogen gas. The sample was then continuously sheared at 100 $sec^{-1}$ while heating to 250° F. At temperature, a rate sweep using 170, 128, 85 and 42 $sec^{-1}$ was made and repeated every 30 minutes. The interim rate between the sweeps was at 100 $sec^{-1}$. The stresses corresponding to each rate of the rate sweep, together with the rates, were converted to their logarithmic value. The Power Law indices, n' and K, were then determined as described by the American Petroleum Institute's Bulletin RP-39. The Power Law indices were used to calculate gels viscosity at 170, 100 and 40 $sec^{-1}$ over time. These data are shown in Table 1. Times indicated are in minutes.

TABLE 1

Temperature (°F): 250
Additives: 2% KCl, 4.8 gr. CMHPG, 0.6 gr. NaHCO$_3$, 1.2 gr. Na$_2$S$_2$O$_3$.5H$_2$O, 1 ml 48% K$_2$CO$_3$
and 0.75 ml crosslinker:
pH$_{before}$: 9.45 pH$_{after}$: 9.00

| | | | | Viscosity at Rates in Sec$^{-1}$ | | |
|---|---|---|---|---|---|---|
| TIME | TEMP | n' | K | 170 | 100 | 40 |
| 4 | 148 | .198 | 106.186 | 173 | 264 | 551 |
| 31 | 244 | .023 | 3.7372 | 252 | 262 | 281 |
| 91 | 245 | 1.039 | 2.0322 | 248 | 243 | 235 |
| 151 | 245 | .98 | 2.4419 | 220 | 223 | 227 |
| 241 | 245 | .965 | 2.4425 | 204 | 208 | 215 |
| 331 | 245 | .92 | 2.7991 | 186 | 194 | 208 |
| 391 | 245 | .945 | 2.3412 | 177 | 182 | 191 |
| 451 | 245 | .964 | 2.0647 | 172 | 175 | 181 |
| 512 | 245 | .951 | 2.1342 | 166 | 170 | 178 |
| 572 | 245 | .947 | 2.1763 | 166 | 170 | 179 |
| 631 | 245 | .944 | 2.0922 | 157 | 162 | 170 |
| 691 | 245 | .924 | 2.3132 | 157 | 163 | 175 |
| 751 | 245 | .908 | 2.3845 | 149 | 156 | 170 |
| 811 | 245 | .913 | 2.2068 | 141 | 148 | 160 |
| 871 | 100 | .618 | 25.2904 | 356 | 435 | 618 |

EXAMPLE 3

A viscous polymer fluid was prepared this time by hydrating 4.8 g of high grade guar gum in 1 liter of 2% (wt/vol) potassium chloride solution. After mixing for 30 minutes, 0.6 g of sodium bicarbonate and 1.2 g of sodium thiosulfate were added. Last, a solution of 0.5 ml crosslinker was prepared as in Example 1. The crosslinker, however, was previously treated with small amounts of ethanolamine to adjust the crosslinker pH to 10.0. This adjustment, together with the sodium bicarbonate, allowed the crosslinker to form a uniform blend in the polymer fluid. Rapid gelation of the fluid would otherwise occur without the addition of the ethanolamine to adjust the pH. As in Example 2, 42 grams of fluid was used to measure the rheological properties of the fluid with the Fann viscometer. The test temperature was maintained at 250° F. Results are shown in Table 2 below.

TABLE 2

Temperature (°F.): 250
Additives: 2% KCl, 4.8 gr. Guar, 0.6 gr NaHCO$_3$, 1.2 gr Na$_2$S$_2$O$_3$.5H$_2$O and 0.50 ml Crosslinker
adjusted pH 10 with Ethanolamine
pH$_{before}$: 8.75

| | | | | Viscosity at Rates in Sec$^{-1}$ | | |
|---|---|---|---|---|---|---|
| TIME | TEMP | n' | K | 170 | 100 | 40 |
| 7 | 202 | 1.065 | 1.864 | 260 | 251 | 23- |
| 37 | 251 | 1.006 | 2.3243 | 240 | 239 | 238 |
| 66 | 250 | .873 | 3.9643 | 206 | 221 | 248 |

TABLE 2-continued

Temperature (°F.): 250
Additives: 2% KCl, 4.8 gr. Guar, 0.6 gr NaHCO$_3$, 1.2 gr Na$_2$S$_2$O$_3$.5H$_2$O and 0.50 ml Crosslinker
adjusted pH 10 with Ethanolamine
pH$_{before}$: 8.75

| TIME | TEMP | n' | K | Viscosity at Rates in Sec$^{-1}$ | | |
|---|---|---|---|---|---|---|
| | | | | 170 | 100 | 40 |
| 96 | 252 | .854 | 3.8164 | 180 | 195 | 223 |
| 126 | 252 | .818 | 4.218 | 166 | 182 | 216 |

EXAMPLE 4

Example 3 was repeated except that the rheological properties were measured at 225° F. These data are presented in Table 3.

TABLE 3

Temperature (°F.): 225
Additives: 2% KCl, 4.8 gr. NaHCO$_3$, 1.2 gr Na$_2$S$_2$O$_3$
and 0.50 ml Crosslinker adjusted pH 10 with Ethanolamine
pH$_{before}$: 8.75

| TIME | TEMP | n' | K | Viscosity at Rates in Sec$^{-1}$ | | |
|---|---|---|---|---|---|---|
| | | | | 170 | 100 | 40 |
| 4 | 142 | .04 | 178.247 | 129 | 214 | 516 |
| 33 | 220 | .93 | 3.0431 | 212 | 220 | 235 |
| 63 | 226 | .869 | 3.4808 | 178 | 190 | 215 |
| 93 | 226 | .834 | 3.6826 | 166 | 181 | 210 |
| 123 | 226 | .773 | 4.6602 | 144 | 163 | 201 |

EXAMPLE 5

Example 3 was repeated except that rheological properties were measured at 200° F. Data are presented in Table 4.

TABLE 4

Temperature (°F.): 200
Additives: 2% KCl, 4.8 gr. Guar, 0.6 gr NaHCO$_3$, 1.2 gr Na$_2$S$_2$O$_3$
and 0.5 ml Crosslinker adjusted to pH 10 with Ethanolamine
pH$_{before}$: 8.70 pH$_{after}$: 8.03

| TIME | TEMP | n' | K | Viscosity at Rates in Sec$^{-1}$ | | |
|---|---|---|---|---|---|---|
| | | | | 170 | 100 | 40 |
| 4 | 125 | .781 | 9.0737 | 295 | 331 | 405 |
| 33 | 196 | 1.166 | 1.5644 | 367 | 336 | 289 |
| 63 | 106 | 1.073 | 2.1296 | 310 | 298 | 279 |
| 123 | 196 | .934 | 3.4528 | 246 | 255 | 271 |
| 213 | 196 | .863 | 3.199 | 158 | 170 | 193 |
| 303 | 196 | .823 | 3.0278 | 122 | 134 | 158 |
| 393 | 196 | .763 | 3.244 | 96 | 109 | 135 |
| 483 | 197 | .741 | 3.092 | 82 | 94 | 119 |
| 549 | 197 | .678 | 3.9055 | 75 | 89 | 119 |
| 609 | 197 | .667 | 3.7567 | 68 | 81 | 110 |
| 669 | 197 | .638 | 4.1037 | 64 | 77 | 108 |
| 759 | 196 | .629 | 3.8746 | 58 | 70 | 99 |
| 819 | 196 | .664 | 3.0915 | 55 | 66 | 90 |
| 879 | 196 | .639 | 3.39 | 53 | 64 | 90 |
| 909 | 93 | .66 | 8.8392 | 154 | 185 | 252 |

The method of the invention allows zirconium compounds, such as zirconium lactate, to be formed without producing undesirable by-products that must be removed by washing and filtering procedures. Because zirconium carbonate is used as the starting material, the reaction results in the production of carbon dioxide gas as a by-product. The carbon dioxide merely bubbles from solution as a gas so that no additional separating techniques are required. This eliminates the loss of product that would otherwise occur during the washing and filtering steps. There is also no chloride to be recovered and disposed of.

While the invention has been shown in only one of its forms, it should be apparent to those skilled in the art that it is not so limited but is susceptible to various changes without departing from the scope of the invention.

I claim:

1. A method of formulating a zirconium compound comprising:

preparing an aqueous solution of lactic acid or lactate salt, heating the solution to a temperature of at least 200° F., then admixing to the solution an amount of zirconium carbonate, wherein the amount of lactic acid or lactate salt combined with zirconium carbonate is in a molar ratio of at least about 3 to 1 and wherein the reacting solution has a pH below about 6, and allowing the solution to react to form a precipitate of the zirconium compound and carbon dioxide gas, and allowing the carbon dioxide gas to evolve from the solution.

2. The method of claim 1, wherein:

the amount of lactic acid or lactate salt combined with zirconium carbonate is in a molar ratio of about 4 to 9 moles lactic acid or lactate salt to about 1 mole of zirconium.

3. The method of claim 1, further comprising:

neutralizing the solution after the reaction is complete by the addition of an alkanolamine in an amount sufficient to dissolve the precipitate.

4. The method of claim 3, wherein:

the alkanolamine is triethanolamine.

5. The method of claim 4, wherein:

the triethanolamine is added in an amount of about 3 moles per mole of zirconium.

6. A method of preparing a zirconium crosslinker for use in crosslinking viscous polymer gels for hydraulic fracturing fluids, the method comprising the steps of:

combining in solution an amount of lactic acid or lactate salt with an amount of zirconium carbonate at a temperature of at least 200° F., wherein the amount of lactic acid or lactate salt combined with zirconium carbonate is in a molar ratio of at least about 3 to 1, and wherein the pH of the reacting solution is below about 6, and allowing the solution to react to form a precipitate of a zirconium compound and carbon dioxide gas, and allowing the carbon dioxide gas to evolve from the solution; and neutralizing the solution with triethanolamine in an amount sufficient to dissolve the precipitate.

7. The method of claim 6, wherein:

the amount of lactic acid or lactate salt combined with zirconium carbonate is in a molar ratio of about 4 to 9 moles lactic acid or lactate salt to about 1 mole zirconium carbonate.

8. The method of claim 6, wherein:

the triethanolamine is added in an amount of about 3 moles per mole of zirconium.

9. A method of fracturing a subterranean formation of a well used in recovering oil or gas, comprising the steps of:

preparing an aqueous polymer fluid;

admixing with the polymer fluid the zirconium crosslinker made by the method of claim 6, and injecting the polymer fluid with the zirconium crosslinker into the well at a high enough rate so that fractures are formed in the formation.

10. A method of formulating a zirconium compound, comprising the steps of:

preparing an aqueous solution of an amount of an alpha-hydroxy carboxylic acid or a salt of an alpha-hydroxy carboxylic acid; and adding an amount of zirconium carbonate to said aqueous solution to form a mixture, wherein said alpha-hydroxy carboxylic acid or a salt of an alpha-hydroxy carboxylic acid comprises at least three moles per one mole of zirconium;

wherein said aqueous solution is heated to a temperature of at least 200° F. before and during the step of adding said zirconium carbonate to said aqueous solution;

wherein said mixture has a pH below about 6; and whereby carbon dioxide is released from the reaction of said alpha-hydroxy carboxylic acid or salt of an alpha-hydroxy carboxylic acid and said zirconium carbonate and wherein a zirconium precipitate is produced.

11. The method of claim 10, further comprising the step of adding a suitable base to said mixture in an amount sufficient to dissolve said zirconium precipitate.

12. The method of claim 11, wherein said suitable base comprises triethanolamine, potassium hydroxide, or ammonium hydroxide.

13. The method of claim 10, wherein said alpha-hydroxy carboxylic acid comprises lactic acid.

14. The method of claim 10, wherein said alpha-hydroxy carboxylic acid or salt of an alpha-hydroxy carboxylic acid is selected from the group consisting of malic acid, a salt of malic acid, citric acid, a salt of citric acid, or a salt of lactic acid.

15. The method of claim 10, wherein said alpha-hydroxy carboxylic acid or salt of an alpha-hydroxy carboxylic acid is present in an amount of about 4 to 9 moles per one mole of zirconium.

16. A method of formulating a zirconium compound, comprising the steps of:

preparing an aqueous solution of lactic acid and water;

heating said aqueous solution to a temperature of approximately 200° F.;

adding an amount of zirconium carbonate to said aqueous solution to form a mixture, wherein the pH of said mixture is below about 6, wherein said lactic acid is present in an amount of about 4 to 9 moles per about one mole of zirconium, wherein a zirconium precipitate is produced and whereby carbon dioxide is released from the reaction of said lactic acid and said zirconium carbonate; and adding triethanolamine to said mixture in an amount sufficient to dissolve said zirconium precipitate.

17. A method of fracturing a subterranean formation of an oil or gas well, comprising the steps of:

preparing an aqueous polymer fluid;

mixing said polymer fluid with the zirconium compound made by the method of claim 16 to form a solution; and injecting said solution into said well at a rate sufficient to form fractures in said subterranean formation.

* * * * *